United States Patent
Knoesche et al.

(10) Patent No.: US 7,342,134 B2
(45) Date of Patent: Mar. 11, 2008

(54) METHOD FOR THE DISTILLATIVE RECOVERY OF TOLUYLENEDIAMINE

(75) Inventors: Carsten Knoesche, Niederkirchen (DE); Martin Sohn, Mannheim (DE); Ulrich Penzel, Tettau (DE); Hans-Juergen Pallasch, Ludwigshafen (DE); Gunter Georgi, Lauchhammer (DE); Wolfgang Mackenroth, Bad Duerkheim (DE); Hans Volkmar Schwarz, Overijse (BE); Stefan Maixner, Schwetzingen (DE); Gerald Molz, Maikammer (DE); Eckhard Stroefer, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 42 days.

(21) Appl. No.: 10/585,648

(22) PCT Filed: Jan. 7, 2005

(86) PCT No.: PCT/EP2005/000081

§ 371 (c)(1),
(2), (4) Date: Jul. 7, 2006

(87) PCT Pub. No.: WO2005/066113

PCT Pub. Date: Jul. 21, 2005

(65) Prior Publication Data

US 2007/0083065 A1    Apr. 12, 2007

(30) Foreign Application Priority Data

Jan. 8, 2004    (DE) .................. 10 2004 001 456

(51) Int. Cl.
*C07C 209/00* (2006.01)
(52) U.S. Cl. .................................... 564/347
(58) Field of Classification Search .................... None
See application file for complete search history.

(56) References Cited

FOREIGN PATENT DOCUMENTS

| DE | 101 00 552 | 7/2002 |
|----|------------|--------|
| GB | 1 303 562  | 1/1973 |
| WO | 94/06752   | 3/1994 |

OTHER PUBLICATIONS

"SRI—Report 1A", pp. 55 to 65, 1968.

*Primary Examiner*—Samuel A Barts
(74) *Attorney, Agent, or Firm*—Oblon, Spivak, McClelland, Maier & Neustadt, P.C.

(57) ABSTRACT

The invention relates to a process for distillatively preparing TDA from a reactant stream comprising TDA, high boilers and low boilers in a dividing wall column in which a dividing wall is disposed in the longitudinal direction of the column to form an upper combined column region (2), a lower combined column region (3), a feed section (4) having a rectifying section (5) and stripping section (6), and also a withdrawal section (7) having a rectifying section (9) and stripping section (8), which comprises the following steps:
  a. feeding the reactant stream (13) into the feed section (4) of the dividing wall column (1);
  b. drawing off a low boiler fraction via the top of the column (11);
  c. drawing off TDA via a side draw (14) in the withdrawal section (7) of the dividing wall column (1);
  d. drawing off a low boiler fraction via the bottom of the column (12).

12 Claims, 1 Drawing Sheet

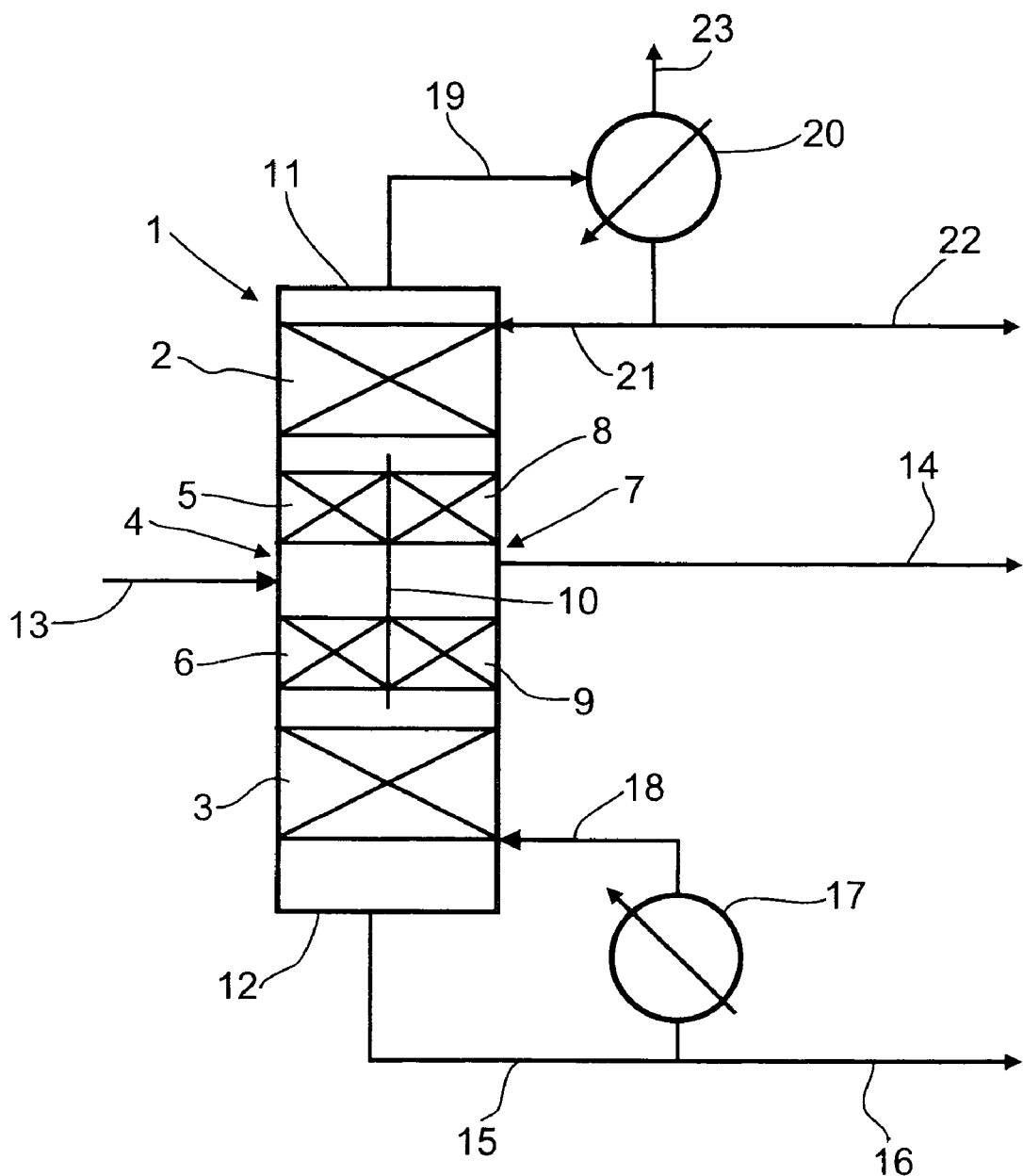

METHOD FOR THE DISTILLATIVE RECOVERY OF TOLUYLENEDIAMINE

The invention relates to a process for distillatively preparing toluylenediamine from a reactant stream comprising toluylenediamine.

Toluylenediamine is an intermediate in the preparation of toluylene diisocyanate. It is used in particular as a monomer in polyurethane production. In addition, toluylenediamine is also used as a dye for hair dyeing.

In the prior art processes for purifying toluylenediamine (TDA) by distillation, the crude TDA obtained in the hydrogenation of dinitrotoluene is initially fed to a rectification column. In the rectification column, the low-boiling constituents are removed overhead. Low-boiling constituents are, for example, 3,4-TDA, ortho-toluidine and water. ortho-Toluidine and water occur merely in traces. The bottoms mixture obtained in the rectification comprises in particular 2,4-TDA, 2,6-TDA and an oligomer mixture which is formed from the TDA isomers present in the bottoms mixture. To remove the product of value comprising 2,4-TDA and 2,6-TDA, the bottoms mixture is fed to a thin-film evaporator. In the thin-film evaporator, the tolylene isomer mixture is removed. Such a process is described, for example, in SRI report 1A, 1968, page 55 to 65.

A further known means of removing the TDA isomer mixture from the bottoms mixture is the use of a second rectification column. Here, the TDA isomer mixture is drawn off over-head. The remaining bottoms which comprise in particular the oligomer mixture formed from the TDA isomers and the catalyst from the hydrogenation are fed to a suitable disposal operation.

A disadvantage of the prior art processes for purifying TDA by distillation is that two apparatus, for example two rectification columns or one rectification column and one thin-film evaporator, have to be provided. A large amount of energy is also required to operate the apparatus.

It is an object of the invention to provide an improved, especially more economically viable, process for purifying TDA by distillation from a reactant stream which is obtained in the hydrogenation of dinitrotoluene and comprises TDA.

The achievement of the object consists in a process for purifying TDA by distillation from a reactant stream comprising TDA, high boilers and low boilers in a dividing wall column in which a dividing wall is disposed in the longitudinal direction of the column to form an upper combined column region (2), a lower combined column region (3), a feed section (4) having a rectifying section (5) and stripping section (6), and also a withdrawal section (7) having a rectifying section (9) and stripping section (8), which comprises the following steps:

A) feeding the reactant stream into the feed section of the dividing wall column;
B) drawing off a low boiler fraction via the top of the column;
C) drawing off TDA via a side draw in the withdrawal section of the dividing wall column;
D) drawing off a high boiler fraction via the bottom of the column.

The reactant stream fed to the dividing wall column preferably contains from 80 to 98% of TDA, from 5 to 15% of low boilers and from 0.5 to 6% of high boilers, more preferably from 85 to 96% of TDA, from 5.5 to 8.5% of low boilers and from 0.5 to 3% of high boilers, and very preferably from 90 to 94% of TDA, from 6 to 6.5% of low boilers and from 1 to 1.8% of high boilers.

TDA means an isomer mixture composed of substantially 2,4-TDA and 2,6-TDA. The TDA isomer mixture preferably contains from 70 to 90% of 2,4-TDA and from 10 to 30% of 2,6-TDA, more preferably from 75 to 85% of 2,4-TDA and from 15 to 25% of 2,6-TDA. Very preferably, the TDA isomer mixture contains from 78 to 82% of 2,4-TDA and from 18 to 22% of 2,6-TDA.

The low boilers are composed substantially of vicinals, water and ortho-toluidine. The low boilers preferably contain from 90 to 100% of vicinals, from 0 to 10% of water and from 0 to 5% of ortho-toluidine, more preferably from 92 to 100% of vicinals, from 0 to 7% of water and from 0 to 2% of ortho-toluidine, and especially from 95 to 100% of vicinals, from 0 to 5% of water and from 0 to 1% of ortho-toluidine.

Vicinals means a mixture of 2,3-TDA and 3,4-TDA. Preference is given to a composition composed of from 20 to 50% of 2,3-TDA and from 50 to 80% of 3,4-TDA, more preferably from 30 to 45% of 2,3-TDA and from 55 to 70% of 3,4-TDA and very preferably from 35 to 40% of 2,3-TDA and from 60 to 65% of 3,4-TDA.

The high boilers are composed substantially of oligomers and polymers which are formed by reaction of the TDA isomers with each other. The oligomers and polymers are substantially secondary or tertiary amines. The oligomers and polymers are substantially azo, azoxy or hydrazine compounds.

The use of a dividing wall column is disclosed, for example, by DE-A 101 00 552 for a process for distillatively preparing 1,6-hexanediol, 1,5-pentanediol and caprolactone.

A dividing wall column in the context of the invention is a distillation column having at least one vertical dividing wall which prevents crossmixing of liquid and vapor streams in subregions. The at least one dividing wall divides the column in longitudinal direction in its middle region into a feed section and a withdrawal section.

In a preferred embodiment, the dividing wall is manufactured as a sheet of a metallic material. Suitable metallic materials are in particular ferrous steels.

In a further embodiment, the dividing wall is manufactured from a nonmetallic material, for example ceramic.

In a further preferred embodiment, internals are disposed in the upper combined column region, in the lower combined column region, in the rectifying section and stripping section of the feed section, and also in the rectifying section and stripping section of the withdrawal section. Suitable internals are, for example, column trays, random packings or structured packings.

Preferred internals are structured packings or random packings. Of these, particular preference is given to sheet metal packings or fabric packings.

For all internals, care has to be taken that they have a low pressure drop. Preference is given to a pressure drop of less than 0.15 bar, more preferably less than 0.1 bar and very preferably of less than 0.05 bar.

The random packings and structured packings preferably have a specific surface area of from 125 to 500 $m^2/m^3$, more preferably from 200 to 300 $m^2/m^3$.

In a preferred embodiment, the dividing wall column has from 20 to 50, more preferably from 25 to 35, theoretic plates.

The division of the number of plates between the individual subregions of the dividing wall column is preferably effected in such a way that the upper combined column region, the rectifying section and stripping section of the feed section, and also the rectifying section and stripping section of the withdrawal section, each have from 5 to 50%, preferably from 20 to 40%, of the total number of theoretic plates of the dividing wall column. The lower combined column region preferably has from 0 to 30% of the total number of theoretic plates of the dividing wall column, and the lower combined column region is very preferably the column bottom.

In a preferred embodiment, the reactant is fed via a side feed in the feed section of the dividing wall column, which is disposed between the stripping section and the rectifying section.

For product withdrawal, a side draw is disposed in the withdrawal section of the dividing wall column between stripping section and rectifying section of the withdrawal section. In one embodiment, the side draw for product withdrawal is disposed at the same height in the dividing wall column as the side feed for the reactant feed.

In a further embodiment, the side draw for product withdrawal is offset by from 0 to 20, preferably by from 5 to 15, theoretical plates from the side feed for the reactant feed.

In a preferred process variant, the liquid distribution in the individual subregions of the dividing wall column can in each case be adjusted separately. This allows the total energy requirement which is required to separate the reactant stream to be minimized.

Particularly advantageously, in the subregions of the feed section of the dividing wall column, the liquid may be introduced to an increased extent in the wall region, and, in subregions of the withdrawal section of the dividing wall column, to a reduced extent in the wall region. This prevents un-desired creep streams and increases the achievable final product purities.

The dividing wall column may be equipped in one or more subregions with structured packings or random packings.

It is possible to configure the dividing wall in the form of loosely inserted subsegments. This leads to a further reduction in costs in the production and assembly of the dividing wall column.

Particularly advantageously, the loose dividing wall may have internal manholes or removable able segments which allow access within the dividing wall column from one side of the dividing wall to the other side.

Especially in the case that packings are used as separating internals, the dividing wall may, in a further embodiment, be equipped with thermal insulation. A particularly favorable design is double-walled with interstitial narrow gas space.

In a preferred embodiment, a portion of the high boiler removed via the column bottom is fed back to the dividing wall column via a side feed in the lower combined column region. This ensures that TDA present in the column bottom gets back into the dividing wall column and can evaporate there from the column bottom. This leads to an improved yield of TDA, since less product of value is drawn off via the column bottom. The portion of the high boiler fraction which is not recycled to the dividing wall column is removed from the distillation process and preferably set to recycling.

In a further process variant, a portion of the low boiler fraction drawn off via the top of the column is fed back to the dividing wall column via a side feed in the upper combined column region. This achieves further stripping of the low boiler fraction in TDA. Just like the partial recycling of the high boiler fraction drawn off via the column bottom, this leads to improved yield of the TDA product of value. The portion of the low boiler fraction which is not recycled into the dividing wall column is removed from the distillation process and preferably sent to recycling.

In a preferred process variant, the distillation of the TDA is carried out at a pressure in the column bottom which is below ambient pressure, preferably below 0.2 bar and especially below 0.1 bar. The bottom temperature in the dividing wall column is preferably below 250° C., more preferably below 230° C. and especially below 220° C. The distillation at a pressure below the ambient pressure reduces the boiling temperature of the TDA. This advantageously leads to a saving in heat energy. In addition, this prevents the TDA from reacting to give oligomers or polymers. This leads to a further improvement in the yield of TDA in the purifying distillation.

A further advantage of the use of the dividing wall column for purifying TDA by distillation in comparison to the prior art processes is that a lower holdup can be realized in the dividing wall column for the same yield. This leads to less TDA oligomerizing and also less TDA reacting to give ortho-toluidine in the distillation. This allows a greater yield of TDA to be achieved with the dividing wall column than in the prior art processes.

The invention is described in detail herein below with reference to a drawing.

The single FIGURE shows a process flow diagram for the purifying distillation of TDA in a dividing wall column.

A dividing wall column for carrying out the process according to the invention for purifying TDA by distillation comprises an upper combined column region 2, a lower combined column region 3, a feed section 4 and a withdrawal section 7. In the embodiment illustrated in the FIGURE, the feed section 4 is divided into a rectifying section 5 and a stripping section 6, and the withdrawal section 7 into a stripping section 8 and a rectifying section 9. Within the dividing wall column 1, the feed section 4 and the withdrawal section 7 are separated by a dividing wall 10.

The dividing wall 10 is preferably manufactured from a metallic material, especially from stainless steel. However, in addition to metallic materials, ceramic is also suitable for manufacturing the dividing wall 10.

To operate the dividing wall column 1, a reactant stream 13 is fed in the feed section 4. The reactant stream 13 is preferably fed between the rectifying section 5 and the stripping section 6 of the feed section 4.

The reactant stream 13 is obtained in the hydrogenation of dinitrotoluene and comprises an isomer mixture composed of substantially 2,4-TDA and 2,6-TDA, vicinals, an oligomer mixture formed from TDA, and also ortho-toluidine and water.

For the improved distillative workup of the reactant stream 13, internals are provided in the upper combined column region 2, in the lower combined column region 3, in the rectifying section 5 and stripping section 6 of the feed section 4, and also in the rectifying section 9 and stripping section 8 of the withdrawal section 7. Suitable internals are, for example, trays, structured packings or random packings.

On the withdrawal section 7, a side draw is preferably disposed between the stripping section 8 and the rectifying section 9, through which a product stream 14 is drawn off. The product stream 14 comprises an isomer mixture composed of substantially 2,4-TDA and 2,6-TDA.

The side draw for the product stream 14 is preferably disposed at the same height as the side feed for the reactant stream 13 or preferably offset from the height of the side feed for the reactant stream 13.

During distillation, the high boilers present in the reactant stream 13 accumulate in the bottom 12 of the dividing wall column 1. The high boilers present in the reactant stream 13 are, for example, the oligomer mixture formed from TDA.

The high boilers are drawn off from the column bottom 12 at a bottom stream 15. A substream stream 18 of the high boiler is preferably recycled to the lower combined column region 3 via a first pump 17 and through a side feed. The fraction which is not recycled to the dividing wall column 1 is removed from the distillation process via a high boiler draw 16.

A top stream 19 comprising low boilers is drawn off via the top 11 of the dividing wall column 1. The low boilers present in the top stream 19 are in particular vicinals, ortho-toluidine and water. The top stream 19 is fed to a pump 20. In the embodiment illustrated in the FIGURE, a gas stream 23 is drawn off from the top stream 19 at the second pump 20. The remaining top stream 19 is divided downstream of the second pump 20. A substream 21 is preferably fed to the upper combined column region 2 and thus recycled to the distillation via a side feed. The remaining low boilers are removed from the distillation process via a low boiler draw 22.

EXAMPLE

A mass flow rate of 5000 kg/h obtained in the hydrogenation of dinitrotoluene is fed to a dividing wall column via a side feed. The reactant stream contains 92.37% by weight of TDA, 6.02% by weight of 3,4-TDA, 0.05% by weight of o-toluidine, 0.13% by weight of water and 1.43% by weight of high boilers. The distillation is carried out at a pressure in the column bottom of 0.07 bar and a bottom temperature of 215° C. In the top of the column, a pressure of 0.07 bar at a temperature of 140° C. is established. The 3,4-TDA, the o-toluidine and the water are drawn off via the top of the column. 4602 kg/h of product stream are drawn off via the side draw in the withdrawal section. The product stream is composed of 99.95% by weight of TDA isomer mixture and 0.05% by weight of low boilers. The TDA isomer mixture contains 80% by weight of 2,4-TDA and 20% by weight of 2,6-TDA.

REFERENCE NUMERAL LIST

1 Dividing wall column
2 Upper combined column region
3 Lower combined column region
4 Feed section
5 Rectifying section
6 Stripping section
7 Withdrawal section
8 Stripping section
9 Rectifying section
10 Dividing wall
11 Top of column
12 Bottom of column
13 Reactant stream
14 Product stream
15 Bottom stream
16 High boiler draw
17 First pump
18 High boiler substream
19 Top stream
20 Second pump
21 Low boiler substream
22 Low boiler draw
23 Gas stream

What is claimed is:

1. A process for distillatively preparing toluylenediamine TDA from a reactant stream comprising TDA, high boilers and low boilers in a dividing wall column in which a dividing wall is disposed in the longitudinal direction of the column to form an upper combined column region, a lower combined column region, a feed section having a rectifying section and stripping section, and also a withdrawal section having a rectifying section and stripping section, which comprises the following steps:
   a. feeding the reactant stream into the feed section of the dividing wall column;
   b. drawing off a low boiler fraction via the top of the column;
   c. drawing off TDA via a side draw in the withdrawal section of the dividing wall column;
   d. drawing off a high boiler fraction via the bottom of the column.

2. The process of claim 1, wherein a portion of the high boiler fraction drawn off via the bottom of the column is fed back to the dividing wall column via a side feed in the lower combined column region.

3. The process of claim 1, wherein a portion of the low boiler fraction drawn off via the top of the column is fed back to the dividing wall column via a side feed in the upper combined column region.

4. The process of claim 1, wherein the reactant feed and the side draw for product withdrawal are disposed at the same height in the dividing wall column.

5. The process of claim 1, wherein the reactant feed and the side draw for product withdrawal are disposed at different height in the dividing wall column.

6. The process of claim 5, wherein the side draw for product withdrawal is offset by from 5 to 15 theoretical plates from the reactant feed.

7. The process of claim 1, wherein the distillation is carried out at a pressure in the column bottom of $\leq 1$ bar.

8. The process of claim 1, wherein the distillation is carried out at a pressure in the column bottom of $\leq 0.2$ bar.

9. The process of claim 1, wherein the distillation is carried out at a pressure in the column bottom of $\leq 0.1$ bar.

10. The process of claim 1, wherein the bottom temperature is below 250° C.

11. The process of claim 1, wherein the bottom temperature is below 230° C.

12. The process of claim 1, wherein the bottom temperature is below 220° C.

* * * * *